(12) United States Patent
Salim

(10) Patent No.: US 8,317,762 B2
(45) Date of Patent: Nov. 27, 2012

(54) SKIN PATCH FOR ABSORBING TOXINS FROM THE BODY

(76) Inventor: Nurman Salim, Shimada (JP)

( * ) Notice: Subject to any disclaimer, the term of this patent is extended or adjusted under 35 U.S.C. 154(b) by 423 days.

(21) Appl. No.: 12/267,731

(22) Filed: Nov. 10, 2008

(65) Prior Publication Data

US 2010/0121297 A1  May 13, 2010

(51) Int. Cl.
*A61F 13/00* (2006.01)
*A61F 13/02* (2006.01)
(52) U.S. Cl. ............... 604/307; 604/304; 604/375
(58) Field of Classification Search .......... 604/304, 604/307, 375
See application file for complete search history.

(56) References Cited

U.S. PATENT DOCUMENTS

| | | | |
|---|---|---|---|
| 2,296,207 A * | 9/1942 | Kittinger | 604/307 |
| 3,056,406 A * | 10/1962 | Ness | 604/381 |
| 3,122,140 A * | 2/1964 | Crowe, Jr. | 604/369 |
| 3,598,122 A * | 8/1971 | Zaffaroni | 424/435 |
| 4,297,995 A * | 11/1981 | Golub | 604/304 |
| 5,480,647 A * | 1/1996 | Tsai | 424/443 |
| 5,782,788 A * | 7/1998 | Widemire | 602/48 |
| 6,168,800 B1 * | 1/2001 | Dobos et al. | 424/405 |
| 6,348,200 B1 * | 2/2002 | Nakajima et al. | 424/401 |
| 7,238,849 B2 * | 7/2007 | Goldberg et al. | 602/48 |
| 2003/0035826 A1 * | 2/2003 | Hosokawa et al. | 424/449 |
| 2004/0002675 A1 * | 1/2004 | Nierle et al. | 602/41 |
| 2005/0058694 A1 * | 3/2005 | Nielsen | 424/445 |
| 2006/0280712 A1 * | 12/2006 | Kuroda et al. | 424/70.12 |

FOREIGN PATENT DOCUMENTS

GB  2416664 A  *  2/2006

OTHER PUBLICATIONS

Gallan, Annie. "Banishing toxins from the body." Quesnel Cariboo Observer. Jan. 2006: A18.*
Schwarcz, Joe. "My name is Joe. I'm in detox. I have patches." The Gazette. Montreal, Que.: May 2007: J11.*
Salim, Nurman. Miracle Patches. Revealing the Healing Powers of Detox Patches, Negative Ion, and Far Infrared Rays. http://healthmarvels.net/pdf/miraclepatches.pdf. 2005.*
Overview of Kenrico Detox Foot Pads/Sap Sheets at http://www.changewitheft.com/detox-foot-pads.html captured on Jan. 11, 2007 (by the Wayback Machine).*
Amazon.com: Customer Reviews: 20 Gold TRMX-2i Kenrico . . . Detox Foot and Body Pads/patches. http://www.amazon.com/TRMX-2i-KENRICO-Upgraded-Tourmaline-ORGANIC/product-reviews/B000MFGL7E.*
Immune Matrix, LLC :: Detox Foot Pads :: GOLD TRMX-2i. https://www.immunematrix.com/store/product.php?productid=16200.*
DetoxFootPads.eu. http://detoxfootpads.eu/varieties.php.*

* cited by examiner

*Primary Examiner* — Loan Thanh
*Assistant Examiner* — Kathryn E Ditmer
(74) *Attorney, Agent, or Firm* — Maier & Maier PLLC

(57) ABSTRACT

A skin patch for absorbing toxins from a body includes a first side having a heat reflective foil. A second side includes a non-woven rayon surface for absorbing the toxins. The rayon surface includes a plurality of openings for enhancing far infrared ray emission into a skin when the second side is placed in contact with the skin. A mixture of natural ingredients includes vinegar, chitosan, loquat leaf, *houttuynia cordata*, vitamin C, tourmaline, vegetable fiber, and dextrin. The mixture is formulated to emit the far infrared emission, whereby blood circulation is promoted and perspiration and any toxins contained therein are absorbed by the rayon surface.

10 Claims, 1 Drawing Sheet

SKIN PATCH FOR ABSORBING TOXINS FROM THE BODY

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates generally to skin patches. More particularly, the invention relates to a skin patch that absorbs toxins from the body using infrared rays.

BACKGROUND OF THE INVENTION

Far infrared rays are thought to have the potential to be used to generate blood circulation in the body. In 1870, Dr. Pleasanton, a researcher in the United States, published research showing the relationship between light frequency and the rate of growth of cells and tissues, as well as their rate of cell division. Also, Dr. Neils Finsen, cured lesions and variola using red and infrared rays.

More recent research performed by Tiina Karu, M.D., of the Laser Technology Center in Russia, holds that this spectrum of light speeds up cellular metabolic processes, such as, but not limited to, stimulating the activity of mitochondria, and triggering enzyme activity as well as the healing, regeneration, and normalization of damaged cell tissue. Sunshine is known to emit far infrared rays. Electricity can also generate far infrared rays. A method of far infrared generation with electricity is disclosed in U.S. Pat. No. 6,610,082. However, the conversion of sunshine or electricity to generate far infrared rays may not be an efficient method for promoting blood circulation and other cellular processes in the body.

In view of the foregoing, there is a need for improved techniques for providing far infrared rays for use in promoting blood circulation and other cellular processes in the body that do not require sunshine or electricity.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1A shows the front of the patch, and FIG. 1B shows the back of the patch; and Table 1 lists an exemplary formula for the natural ingredients in a toxin-absorbing patch, according to an embodiment of the present invention.

Figure 1A:
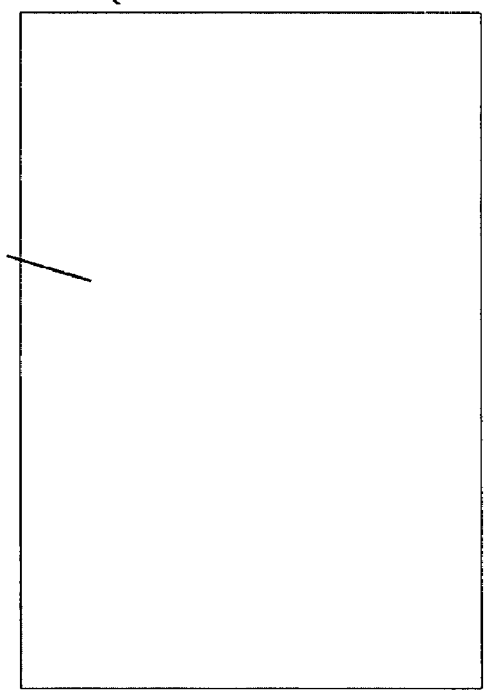
FIGS. 1A and 1B illustrate an exemplary toxin-absorbing patch, in accordance with an embodiment of the present invention.

Unless otherwise indicated illustrations in the figures are not necessarily drawn to scale.

SUMMARY OF THE INVENTION

To achieve the forgoing and other objects and in accordance with the purpose of the invention, a skin patch for absorbing toxins from the body is presented.

In one embodiment, a skin patch for absorbing toxins from a body is presented. The skin patch includes a first side having a heat reflective foil. A second side includes a non-woven rayon surface for absorbing the toxins. The rayon surface includes a plurality of openings for enhancing far infrared ray emission into a skin when the second side is placed in contact with the skin. A mixture of natural ingredients including vinegar, chitosan, loquat leaf, *houttuynia cordata*, vitamin C, tourmaline, vegetable fiber, and dextrin. The mixture is formulated to emit the far infrared emission, whereby blood circulation is promoted and perspiration and any toxins contained therein are absorbed by the rayon surface.

In another embodiment a skin patch for absorbing toxins from a body is presented. The skin patch includes means for reflecting heat, means for absorbing the toxins, means for enhancing far infrared ray emissions into a skin and means for emitting the far infrared ray emissions, whereby blood circulation is promoted and perspiration and any toxins contained therein are absorbed by the absorbing means.

Other features, advantages, and object of the present invention will become more apparent and be more readily understood from the following detailed description, which should be read in conjunction with the accompanying drawings.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention will now be described in detail with reference to embodiments thereof as illustrated in the accompanying drawings.

Preferred embodiments of the present invention provide a toxin-absorbing patch that is used to generate far infrared rays from natural ingredients without the help of electricity and sunshine. Exemplary purposes of preferred embodiments of the present invention are to help improve blood circulation and to reduce waste and toxins in the body. In a preferred embodiment, a toxin-absorbing patch comprises powdered herbal ingredients. The patch is applied to the sole of a foot and emits far infrared rays onto the foot that causes the foot to perspire during application. The warmth from the far infrared rays helps improve blood circulation, and the perspiration absorbed into the patch may contain toxic waste such as, but not limited to, heavy metals. In preferred embodiments, the patch is easy to apply and works in six to eight hours of time. This allows for use during bedtime. In preferred embodiments, adhesive tape or a bandage is used to secure the toxin absorbing patch onto the skin.

Figure 1B:
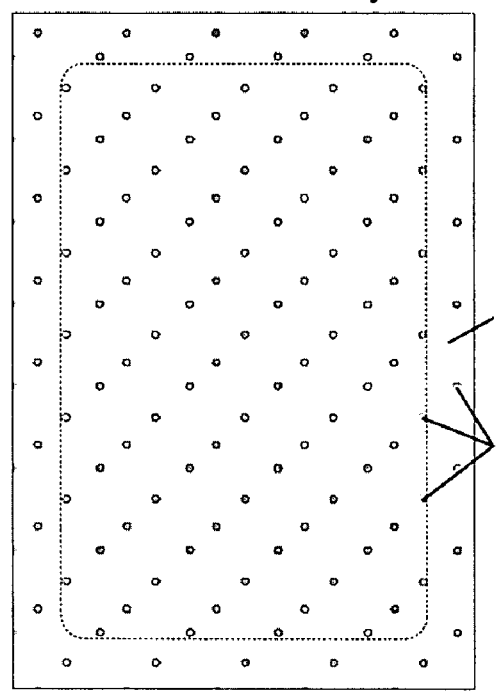

FIGS. 1A and 1B illustrate an exemplary toxin-absorbing patch 100, in accordance with an embodiment of the present invention. FIG. 1A shows the front of patch 100, and FIG. 1B shows the back of patch 100. The front section of patch 100 is made from thin-layered titanium foil 103, and the rear section of patch 100 is made from non-woven rayon 105. Foil 103 provides a very smooth, shiny and reflective surface, which can reflect heat. Adhesive tape is applied to foil 103 on the front section of patch 100 for application. Rayon 105 on the rear section of patch 100 is applied directly onto the skin during use. Rayon 105 comprises openings 107 that offer enhanced far infrared ray emission into the skin. Patch 100 preferably has a width of 60 mm and a length of 80 to 90 mm; however, patches in alternate embodiments may be various shapes and sizes. Patch 100 has large surface area so that it can cover a large section of the body. The weight of patch 100 is preferably five grams with an error level of 0.2 grams; however, patches in alternate embodiments may weigh more or less.

In the present embodiment, powdered natural ingredients are sealed inside patch 100 between foil 103 and rayon 105. Patch 100 comprises a sachet between foil 103 and rayon 105 that has a bag opening into which the natural ingredients such as, but not limited to, vinegar, chitosan, loquat leaf, *houttuynia cordata*, vitamin C, tourmaline, vegetable fiber, and dextrin may be inserted. In the present embodiment, the bag section of the sachet is large and can be made to contain five to eight grams of ingredients. This mixture of natural ingredients is formulated to emit heat, or far infrared rays. Table 1 lists an exemplary formula for the natural ingredients in a toxin-absorbing patch, according to an embodiment of the present invention. Those skilled in the art, in light of the present teachings, will readily recognize that various other types of ingredients and amounts of ingredients may be used in alternate embodiments.

In typical use of the present embodiment, patch 100 is applied externally on the surface of the skin. Patch 100 is attached to a bandage or adhesive tape before application to the skin. A user applies patch 100 to the skin by joining patch 100 to the bandage or adhesive tape with the edges of the bandage or adhesive tape extending beyond the edges of patch 100 and then attaching patch 100 with the adhesive tape or bandage to any location on the body that requires far infrared rays. Typically, the user applies patch 100 onto the bottom of a foot for six to eight hours. This allows for use during bedtime. During use, the foot produces sweat due to the heat coming from patch 100, and the sweat may include toxins such as, but not limited to, heavy metals, which are absorbed into patch 100. Therefore, a user that is suffering from heavy metal toxicity, for example, without limitation, a person with Autism, may benefit from the use of patch 100 because of the heavy metal reduction capability. The warmth from the far infrared rays also may help to improve blood circulation, and people suffering from blocked blood circulation may benefit from using patch 100. In the present embodiment, patch 100 fits virtually any part of the body, is easy to use, and generally eliminates the need for electrical devices and interference. Patch 100 is made of non-allergic material, and may therefore be used by people who have allergies.

Testing has shown that patches according to embodiments of the present invention may be used to emit heat when comprising a correct mixture of natural ingredients. Previously, only devices using electrical currents could be used to generate far infrared emission. Furthermore, an analysis of a new toxin-absorbing patch and a used toxin-absorbing patch was performed by Japan Food Research Laboratories on Dec. 2, 2005. The analysis tested for various heavy metals in the two patches including arsenic, lead, cadmium, mercury, tin, cobalt, and chromium. In the analysis only 0.01 parts per million (ppm) of cadmium was detected and none of the other metals were detected in the new patch while 0.55 ppm of lead, 0.03 ppm of cadmium, 0.09 ppm of cobalt, and 1.7 ppm of chromium were detected in the used patch. This analysis provides evidence that embodiments of the present invention may be used for the absorption of heavy metal from the body into the patch.

Having fully described at least one embodiment of the present invention, other equivalent or alternative methods of providing toxin absorption and improving blood circulation using far infrared rays according to the present invention will be apparent to those skilled in the art. The invention has been described above by way of illustration, and the specific embodiments disclosed are not intended to limit the invention to the particular forms disclosed. For example, the particular implementation of the patch may vary depending upon the intended location of application. The patches described in the foregoing were directed to implementations typically applied to the bottom of the foot; however, similar techniques are to provide patches that are shaped to specifically fit on various parts of the body. For example, without limitation, large sheets may be used on the back or the back of the legs, curved patches may be used on the underarms, and small, round patches may be used on the hands. Implementations of the present invention that are applied to various areas of the body are contemplated as within the scope of the present invention. The invention is thus to cover all modifications, equivalents, and alternatives falling within the spirit and scope of the following claims.

TABLE 1

| Ingredient | Amount |
| --- | --- |
| Wood Vinegar | 0.60 grams |
| Bamboo Vinegar | 0.60 grams |
| Chitosan | 0.04 grams |
| Loquat Leaf | 0.04 grams |
| Dokudami: Houttuynia Cordata | 0.04 grams |
| Vitamin C | 0.04 grams |
| Tourmaline | 3.00 grams |
| Vegetable fiber | 0.20 grams |
| Dextrin | 0.44 grams |
| Total: | 5.00 grams |

What is claimed is:

1. A skin patch for absorbing toxins from a body comprising:

a first side comprising a heat reflective foil comprising titanium;

a second side comprising a non-woven rayon surface configured for absorbing and retaining the toxins, said rayon surface comprising a plurality of openings configured for enhancing transmission of far infrared ray emission into a skin when said second side is placed in contact with the skin; and a mixture of natural ingredients consisting of, by weight, 24% vinegar, 0.8% chitosan, 0.8% loquat leaf, 0.8% *houttuynia cordata,* 0.8% vitamin C, 60% tourmaline, 4% vegetable fiber, and 8.8% dextrin, said mixture formulated to emit said far infrared ray emission, whereby blood circulation is promoted and perspiration and any toxins contained therein are absorbed by said rayon surface.

2. The skin patch as recited in claim 1, wherein said heat reflective foil comprises a thin-layered titanium foil.

3. The skin patch as recited in claim 1, wherein said natural ingredients are sealed between said first side and said second side.

4. The skin patch as recited in claim 1, wherein the skin patch is comprised of non-allergic materials.

5. The skin patch as recited in claim 1, wherein the skin patch is generally rectangular in shape.

6. The skin patch as recited in claim 1, wherein the skin patch is operable to be joined to the skin with an adhesive.

7. The skin patch as recited in claim 6 wherein said adhesive is a tape applied to said first side.

8. The skin patch as recited in claim 1, wherein the skin patch is operable to be joined to the skin of a bottom of a foot.

9. A skin patch for absorbing toxins from a body comprising:

means for reflecting heat from far infrared ray emissions;

means for absorbing and retaining the toxins;

means for enhancing transmission of far infrared ray emissions into a skin; and means for emitting said far infrared ray emissions, whereby blood circulation is promoted and perspiration and any toxins contained therein are absorbed by said absorbing means;

wherein said skin patch contains a mixture of natural ingredients consisting of by weight, 24% vinegar, 0.8% chitosan, 0.8% loquat leaf, 0.8% *houttuynia cordata,* 0.8% vitamin C, 60% tourmaline, 4% vegetable fiber, and 8.8% dextrin.

10. The skin patch as recited in claim 9, further comprising means for joining the skin patch to the skin.

* * * * *